(12) United States Patent
Chen et al.

(10) Patent No.: US 6,451,883 B1
(45) Date of Patent: Sep. 17, 2002

(54) PRESSURE SENSITIVE ADHESIVE COMPOSITION

(75) Inventors: Fei Chen, Lynge; Danuta Ciok, Nivaa, both of (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/485,697

(22) PCT Filed: Aug. 27, 1998

(86) PCT No.: PCT/DK98/00368

§ 371 (c)(1),
(2), (4) Date: Feb. 28, 2000

(87) PCT Pub. No.: WO99/11302

PCT Pub. Date: Mar. 11, 1999

(30) Foreign Application Priority Data

Aug. 29, 1997 (DK) ................................................ 0993/97

(51) Int. Cl.⁷ .............................. C08J 5/10; C08L 25/04
(52) U.S. Cl. ........................... 524/31; 523/111; 524/22; 524/31; 524/25; 524/47; 524/503
(58) Field of Search ............................ 523/111; 524/22, 524/31, 25, 47, 45, 503

(56) References Cited

U.S. PATENT DOCUMENTS

| | | | |
|---|---|---|---|
| 3,339,549 A | 9/1967 | Morse | 128/290 |
| 4,192,785 A | 3/1980 | Chen et al. | 260/17.4 |
| 4,231,369 A | 11/1980 | Sorensen et al. | 128/283 |
| 4,367,732 A | 1/1983 | Poulsen et al. | 128/156 |
| 4,477,325 A | 10/1984 | Osburn | 204/159.12 |
| 4,496,357 A | 1/1985 | Osburn | 604/336 |
| 4,551,490 A | 11/1985 | Doyle et al. | 524/22 |
| 5,492,943 A | 2/1996 | Stempel | 523/111 |

FOREIGN PATENT DOCUMENTS

| | | |
|---|---|---|
| EP | 0 081 907 | 6/1983 |
| EP | 0 122 344 | 7/1987 |
| EP | 0 340 945 | 11/1993 |
| GB | 2 300 195 | 10/1996 |

*Primary Examiner*—James J. Seidleck
*Assistant Examiner*—U. K. Rajguru
(74) *Attorney, Agent, or Firm*—Jacobson Holman, PLLC

(57) ABSTRACT

A pressure sensitive adhesive composition suitable for medical purposes comprising a rubbery elastomeric base and one or more water soluble or water swellable hydrocolloids, the adhesive composition comprising a substantially homogeneous mixture of 35–50% of one or more polybutenes, 5–20% of one or more styrene copolymers, and 20–60% of one or more hydrocolloids has very good properties as an adhesive for ostomy appliances.

12 Claims, No Drawings

PRESSURE SENSITIVE ADHESIVE COMPOSITION

BACKGROUND OF THE INVENTION

1. Field of the Invention

The present invention relates to pressure sensitive adhesive compositions suitable for various medical applications and especially suitable for use for adhesion to the skin, in particular in the field of ostomy care. More specifically, this invention relates to adhesive compositions comprising a rubbery elastomeric base and one or more water soluble or water swellable hydrocolloids dispersed therein, the use of such adhesive compositions for the preparation of a wound dressing or an adhesive wafer for an ostomy appliance, and to wound dressings or ostomy appliances comprising such adhesive composition.

2. Description of the Related Art

Various skin adhesive agents are used today for the above mentioned purposes.

A very widespread embodiment of skin adhesive agents comprises a self-adhesive elastomeric matrix, in which water-absorbing, swelling particles, the so-called hydrocolloids, are dispersed.

Adhesive compositions comprising hydrocolloids have been known for many years. U.S. Pat. No. 3,339,549 discloses a blend of a rubbery elastomer such as polyisobutylene and one or more water soluble or water swellable hydrocolloids such as a powdery mixture of pectin, gelatine and carboxymethylcellulose. The adhesive mass has a water-insoluble film applied to one surface. A composition of this type is available commercially from E.R. Squibb & Sons Inc. under the trademark "Stomadhesive" and is used as a skin barrier around stomas to prevent skin breakdown by the corrosive fluids discharged by the stoma.

In adhesive compositions of this type, the polyisobutylene is responsible for providing of the adhesive properties and the dispersed hydrocolloid powders absorb fluid and render the adhesive agent capable of also adhering to moist skin (wet tack). These compositions are also gaining increasing acceptance as wound dressings for dermal ulcers, burns and other exuding wounds. One major problem which has been encountered with conventional adhesive compositions comprising hydrocolloids is their susceptibility to breakdown upon exposure to body fluids. When the compositions are used as skin barriers, e.g., around stomas, absorption of fluid is desirable, but excessive swelling causes the compositions to lose their integrity by opening for leaks and the barrier must be replaced more often than is desirable from a skin protection point of view, and very often, a residue remains on the skin, which in many cases is difficulty to remove.

A number of attempts have been made to improve the properties of adhesive compositions in order to overcome the above-mentioned drawbacks.

U.S. Pat. Nos. 4,192,785 and 4,551,490 describe incorporating into an adhesive composition of a cohesive strengthening agent such as a natural or synthetic fibrous material, finely divided cellulose, cross-linked dextran, cross-linked carboxymethylcellulose or a starch-acrylonitrile graft copolymer. The cohesive strengthening agent is stated to control the rate of hydration of the composition thereby increasing the resistance against breakdown by body fluids.

U.S. Pat. No. 4,477,325 describes incorporation of a mixture of a copolymer resin of ethylene and vinyl acetate (EVA) into the adhesive composition. After mixing and moulding, the composition is subjected to ionising radiation to form a cross-linked polymer network of the EVA or comprising EVA and another cross-linked resin. The cross-linked matrix is said to provide a controlled swelling.

U.S. Pat. No. 4,496,357 describes the incorporation of fumed silica into adhesive compositions to control swelling.

EP Patent No. 0 122 344 B1 describes incorporation of one or more natural or synthetic polymers capable of developing elastomeric properties when hydrated, such as gluten and long chain polymers of methyl vinyl ether/maleic acid, into the adhesive composition. The adhesive composition is stated to be resistant to erosion by moisture and body fluids.

EP Patent No. 0 340 945 B1 describes incorporation of some polycationic hydrocolloid particles into a hydrocolloid composition. The mixture of polycationic, polyanionic and neutral hydrocolloids is stated to provide increased integrity without a concomitant decrease in absorbing capacity.

In other embodiments, styrene copolymers have been incorporated which is disclosed in a number of patent references.

In U.S. Pat. No. 4,231,369 Sorensen et al. disclose an ostomy skin barrier consisting of a styrene copolymer having dispersed therein a water soluble hydrocolloid gum and a tackifier.

In U.S. Pat. No. 4,367,732 Poulsen et al. disclose an ostomy skin barrier consisting of a water soluble hydrocolloid dispersed in a continuous phase consisting of a styrene copolymer, a hydrocarbon tackifier, and a plasticizer, an antioxidant, and an oily extender.

U.S. Pat. No. 4,551,490 (Doyle et al.) discloses medical grade pressure sensitive adhesive compositions comprising a homogeneous mixture of 5–30% of one or more polyisobutylenes, 3–20% of one or more styrene radial or block type copolymers, mineral oil, one or more water soluble hydrocolloid gums, and a tackifier. One or more water swellable cohesive strengthening agents, an antioxidant, and various other optional ingredients also may be included within the adhesive composition.

EP Patent Publication No. 81907 discloses an ostomy appliance comprising a skin barrier (A) surrounding the stoma and a coupling element (B) including an outwardly extending flange permanently affixed to the skin barrier (A) and a microporous adhesive layer (C) having an upper porous layer. The skin barrier adhesive (A) comprises a homogeneous 30–70% of a blend of low molecular weight polyisobutylene and one or more optional thermoplastic elastomers selected from medium molecular weight polyisobutylene, butyl rubber, and styrene isoprene copolymers and having dispersed therein 35–65% of one or more water soluble hydrocolloids and one or more water swellable or inert cohesive strengthening agents.

Generally speaking, these prior methods are superior to improve the integrity of adhesive compositions. Nevertheless, a need still exists for better adhesive compositions having resistance to biological fluids as well as the properties of improved adhesion to the skin and strechability.

Now it has been found that an improved adhesive composition having resistance to biological fluids as well as the properties of improved adhesion to the skin and strechability may be obtained.

BRIEF SUMMARY OF THE INVENTION

The present invention relates to a pressure sensitive adhesive composition suitable for various medical applications and especially suitable for use for adhesion to the skin, in particular in the field of ostomy care. More specifically, this invention relates to adhesive compositions comprising a rubbery elastomeric base in which one or more water soluble or water swellable hydrocolloids are dispersed, ostomy appliances comprising such adhesive compositions and the use of such adhesive compositions for preparing wound dressings or ostomy appliances.

DETAILED DESCRIPTION OF THE INVENTION

The present invention relates to a pressure sensitive adhesive composition suitable for medical purposes comprising a rubbery elastomeric base and one or more water soluble or water swellable hydrocolloids, the adhesive composition comprising a substantially homogeneous mixture of 35–50 % of one or more polybutenes, 5–20% of one or more styrene copolymers, and 20–60% of one or more hydrocolloids, wherein the mixture of one or more polybutenes and one or more styrene copolymers and one or more hydrocolloids constitutes the adhesive composition.

Without limiting the invention to any hypothesis it is believed that the combination of the styrene radial or block copolymer component and one or more polybutenes in the proportions stated above provides extensibility and both rapid and complete recovery from modular strains to the composition. The combination of the adhesive properties of the polybutenes and the absorbing properties of the hydrocolloids renders the adhesive composition of the invention especially suitable for use in ostomy appliances.

It is preferred that the styrene copolymer is a styrene-butadiene-styrene block copolymer or a styrene-isoprene-styrene block copolymer. Preferably, one or more styrene-isoprene-styrene (SIS) block type copolymers are employed.

The amount of styrene block-copolymer is preferably from 5 to 20% of the total adhesive composition.

The butene component is suitably a conjugated butadiene polymer selected from polybutadiene and polyisoprene.

The Flory molecular weight of the polybutenes to be used according to the invention is preferably from 50,000 to 60,000.

The polybutenes are preferably present in an amount of from 35–50% of the total adhesive composition.

Suitable hydrocolloids for incorporation in the adhesive compositions of the invention are selected from naturally occurring hydrocolloids, semisynthetic hydrocolloids and synthetic hydrocolloids.

More particularly, the hydrocolloids are preferably selected from guar gum, locust bean gum (LBG), pectin, alginates, gelatine, xanthan and/or gum karaya; cellulose derivatives (e.g., salts of carboxymethylcellulose such as sodium carboxymethylcellulose, methylcellulose and hydroxypropylmethylcellulose) and/or sodium starch glycolate and/or polyvinylalcohol and/or polyethylene glycol.

It is preferred to use a combination of two or more hydrocolloids. It is especially preferred to use a combination of pectin, gelatine and carboxymethylcellulose as the hydrocolloid component.

The total amount of hydrocolloids is preferably 30–50% of the total composition. An especially preferred composition according to the invention comprises 50% of a mixture of polyisibutylene and SIS and 50% of a mixture of hydrocolloids comprising gelatine, pectin and CMC.

In a preferred embodiment of the invention for use in an ostomy appliance, the adhesive component of the adhesive composition is a "Swiss roll" adhesive of the kind disclosed in WO 89/05619, the other, more absorbing, component, e.g. comprising a mixture of PIB and a hydrocolloid or any other suitable adhesive.

In a further aspect, the invention relates to the use of an adhesive composition comprising a rubbery elastomeric base and one or more water soluble or water swellable hydrocolloids, the adhesive composition comprising a substantially homogeneous mixture of 35–50 % of one or more polybutenes, 5–20% of one or more styrene copolymers, and 20–60% of one or more hydrocolloids, wherein the mixture of one or more polybutenes and one or more styrene copolymers and one or more hydrocolloids constitutes the adhesive composition, for securing ostomy appliances to the skin and for sealing around an ostomy, for securing wound dressings or wound drainage bandages to the skin, for securing devices for collecting urine to the skin, or for securing orthoses or prostheses to the skin.

In a still further aspect, the invention relates to an ostomy appliance for placing on the abdomen of a patient for use in collecting discharge of visceral contents comprising an adhesive composition containing a rubbery elastomeric base and one or more water soluble or water swellable hydrocolloids, the adhesive composition comprising a substantially homogeneous mixture of 35–50 % of one or more polybutenes, 5–20% of one or more styrene copolymers, and 20–60% of one or more hydrocolloids.

The ostomy appliance according to the invention may be an open or a closed appliance suitable for use in connection with a colostomy, an ileostomy or a urostomy. It may be a one-piece appliance or a body side member or face plate forming part of a two-piece appliance comprising the body side ostomy member and a separate collection bag. A separate collection bag may be attached to the body side member in any convenient manner known per se, e.g., via a coupling ring or by a flange covered with an adhesive.

An ostomy appliance according to the invention may be made from materials conventionally used for the preparation of ostomy appliances in a manner known *per se* in the field.

The invention is illustrated more in detail in the below Examples disclosing embodiments of the invention.

MATERIALS AND METHODS

PIB: Polyisobutylene available under the trademark Vistanex from Exxon Chemical Co. as grade LM-MH.

Kraton D1107: Styrene-isoprene-styrene copolymer having a molecular weight of 212,000–260,000 (GPC) and a content of diblock 15–25%.

Getatine: Gelatine P.S.98.240.233 available from ED. Geistlich Sohne AG.

Pectin: Pectin LM 12CG Z or Pectin USP/100 from Copenhagen Pectin A/S.

CMC: Sodium carboxymethylcellulose available from Akzo under the tradename Akucell® AF2881 or from Hercules Corp. under the trademark Blanose® 9H4XF.

A Z mixer Type LKB 025 from Herman-Linden was used.

EXPERIMENTAL PART

Example 1

Preparation of an Adhesive Material According to the Invention

An adhesive composition having the composition stated in the below table 1 was produced.

TABLE 1

| Ingredient | Percent by weight |
| --- | --- |
| PIB | 41.5 |
| Kraton D1107 (SIS) | 8.5 |
| Gelatine | 17.5 |
| Pectin | 10 |
| CMC | 22.5 |

100 grams of PIB was added to a Z mixer at 150° C. and softened for 5 minutes.

Then 100 grams of Kraton® D1107 was added and mixing was continued at 150° C. and 50 mbar until the blend was homogeneous. The mass was cooled to 80° C., and 166 grams of the mass was removed from the mixer. To the remaining mass was added 66 grams of PIB, 35 grams of gelatine, 20 grams of pectin and 45 grams of CMC. Mixing was continued under 80° C. and 50 mbar until a homogeneous dough-like mixture was obtained.

While still hot and soft, the resulting dough-like mass was then removed from the mixer and formed into sheet stock material having a thickness of approximately 1 mm by compression moulding the adhesive mass at approximately 90° C. and 100 Bar between two sheets of silicone release paper. The resultant flat plate was then cut into pieces having the desired shapes.

The adhesive composition may be used for securing ostomy appliances to the skin and for sealing around an ostomy, for securing wound dressings or wound drainage bandages to the skin, for securing devices for collecting urine to the skin, or for securing orthoses or prostheses to the skin. The ostomy appliances or wound dressings may be any such product known *per se* and may be prepared in a manner analogous to the preparation of similar products using conventional adhesive compositions.

Examples 2–9

Following the procedure of Example 1 adhesive compositions having the compositions stated in the below Tables 2 and 3 were prepared.

TABLE 2

| Ingredient | Example 2 | Example 3 | Example 4 | Example 5 |
| --- | --- | --- | --- | --- |
| PIB | 40 | 45 | 35 | 50 |
| Kraton ® D1107 | 10 | 5 | 15 | 10 |
| Gelatine | 17.5 | 17.5 | 17.5 | 10 |
| Pectin pomosin | 10 | 10 | 10 | 20 |
| CMC | 22.5 | 22.5 | 22.5 | 10 |

TABLE 3

| Ingredient | Example 6 | Example 7 | Example 8 | Example 9 |
| --- | --- | --- | --- | --- |
| PIB | 50 | 42.5 | 37.5 | 45 |
| Kraton ® D1107 | 20 | 12.5 | 17.5 | 15 |
| Gelatine | 10 | 15 | 15 | 10 |
| Pectin pomosin | 10 | 15 | 15 | 10 |
| CMC | 10 | 15 | 15 | 20 |

Example 10

Comparison of colostomy bags having an adhesive wafer comprising an adhesive according to the invention with commercially available bags.

In an open, multi-center, cross-over clinical trial Naturess ostomy bag (ConvaTec) and 1 piece Dansac Light ostomy bag (Dansac AIS) were compared with colostomy bags having an adhesive wafer comprising an adhesive according to the invention having the composition as stated in Example 2 with the purpose to compare the performance of the adhesive.

Inclusion Criteria

The following test persons were eligible for inclusion into the study:

Colostomists who for at least 1 month had been discharged from the hospital and were:
More than 18 years of age;
Capable of giving written informed consent;
Able to complete the registration forms;
In good general health Exclusion Criteria The following were ineligible for inclusion into the study:

Colostomists with severe skin problems and undergoing treatments;
Colostomists who were pregnant or breast feeding.

The following parameters were evaluated:

Wear time, reason for removal, and the immediate adhesion, flexibility, pain at removal, residues—outer section, and residues—inner section according to a scale 1–5, where 5 is best:

In connection with application of the adhesive the immediate adhesion to the skin was rated as:

The immediate adhesion to the skin and flexibility were rated as:

5=Excellent
4=Moderate
3=Acceptable
2=Poor
1=Very poor

The pain at removal, the residues on skin from the outer section of the adhesive and the residues on skin around the stoma from the inner section of the adhesive were rated as:

5=Not at all
4=A little
3=Acceptable
2=Some
1=Very much

The results are summarised in the below Tables 4 and 5.

TABLE 4

Comparison of adhesive according to the invention with adhesive of Naturess ostomy bag (in total 67 ostomates).

| Efficacy Parameter | Bag with adhesive according to invention | Naturess ostomy bag | P-value |
| --- | --- | --- | --- |
| The wear time | 12.79 hours | 12.82 hours | 0.941 |
| The reason for removal | | | |
| Usual routine | 29.4% | 22.9% | 0.039* |
| Hygiene | 58.4% | 52.9% | 0.497 |
| Leakage under adhesive | 8.1% | 8.4% | 0.766 |
| Adhesive partly not sticking | 6.3% | 6.7% | 0.888 |
| Adhesive not sticking at all | 0.4% | 0.2% | 0.564 |
| Skin irritation | 4.3% | 12.7% | 0.027 |
| The immediate adhesion | 4.16 | 3.52 | 0.00007* |
| Flexibility | 4.25 | 3.82 | 0.0003* |

TABLE 4-continued

Comparison of adhesive according to the invention with adhesive of Naturess ostomy bag (in total 67 ostomates).

| Efficacy Parameter | Bag with adhesive according to invention | Naturess ostomy bag | P-value |
| --- | --- | --- | --- |
| Pain at removal | 4.74 | 4.29 | 0.001* |
| Residues - outer section | 4.79 | 4.55 | 0.021* |
| Residues - around stoma | 4.82 | 4.51 | 0.003* |

*Significant difference ($\alpha$ = 0.05) in the Friedman test or in the Wilcoxon signed rank test
% is in % of all used bags

TABLE 5

Comparison of adhesive according to the invention with adhesive of 1 piece Dansac Light ostomy bag (in total 80 ostomates).

| Efficacy Parameter | Bag with adhesive according to invention | 1 piece Dansac Light ostomy bag | P-value |
| --- | --- | --- | --- |
| The wear time | 10.88 hours | 10.11 hours | 0.101 |
| The reason for removal | | | |
| Usual routine | 62.0% | 54.3% | 0.035* |
| Hygiene | 43.1% | 46.4% | 0.434 |
| Leakage under adhesive | 4.0% | 5.3% | 0.574 |
| Adhesive partly not sticking | 4% | 7.4% | 0.203 |
| Adhesive not sticking at all | 0.5% | 0.2% | 0.655 |
| Skin irritation | 1.1% | 4.3% | 0.127 |
| The immediate adhesion | 4.38 | 4.14 | 0.041* |
| Flexibility | 4.20 | 4.16 | 0.741 |
| Pain at removal | 4.71 | 4.00 | 0.00003* |
| Residues - outer section | 4.70 | 4.23 | 0.001* |
| Residues - around stoma | 4.77 | 4.48 | 0.011* |

*Significant difference ($\alpha$ = 0.05) in the Friedman test or in the Wilcoxon signed rank test
% is in % of all used bags Conclusion For the adhesive according to the invention, it is noticed that the adhesive has a better immediate adhesion, it resists the wash out both at the inner and the outer edges and still it is less painful to remove than the known products. These differences are statistically significant.

No significant difference was found concerning the wear time.

For the reason to change, a significant difference was found for "usual routine" in favor of the bags having the adhesive according to the invention Thus, a bag according to the invention can remain on the skin as long as the ostomate wishes.

No significant difference was found concerning the flexibility, between the adhesive of the bag of the invention and the Dansac bag whereas the adhesive of the bag of the invention was more flexible than the adhesive on the Naturess bag.

What is claimed is:

1. A pressure sensitive adhesive composition suitable for medical purposes consisting of a homogenous mixture of 25% by weight—60% by weight of one or more polybutenes having a Flory molecular weight from 50,000 to 60,000, 3% by weight—35% by weight of one or more styrene copolymers, and 20% by weight—60% by weight of one or more hydrocolloids of the total weight of the adhesive composition.

2. The adhesive composition as claimed in claim 1 wherein the styrene copolymer is a styrene-butadiene-styrene block copolymer or a styrene-isoprene-styrene block copolymer.

3. The adhesive composition as claimed in claim 2 wherein the styrene copolymer is a styrene-isoprene-styrene block copolymer.

4. The adhesive composition as claimed in claim 1 wherein the butenes are conjugated butadiene polymer selected from the group consisting of polybutadiene and polyisoprene.

5. The adhesive composition as claimed in claim 1 wherein the hydrocolloids are selected from the group consisting of naturally occurring hydrocolloids, semisynthetic hydrocolloids and synthetic hydrocolloids.

6. The adhesive composition as claimed in claim 5 wherein the hydrocolloids are selected from the group consisting of guar gum, locust bean gum (LBG), pectin, alginates, gelatine, xanthan and gum karaya and mixtures thereof; cellulose derivatives, sodium starch glycolate, polyvinylalcohol and polyethylene glycol and mixtures thereof.

7. An ostomy appliance for placing on the abdomen of a patient for use in collecting discharge of visceral contents comprising an adhesive composition containing a rubbery elastomeric base and one or more water soluble or water swellable hydrocolloids, said adhesive composition consisting of a homogeneous mixture of 25% by weight—60% by weight of one or more polybutenes having a Flory molecular weight from 50,000 to 60,000, 3% by weight—35% by weight of one or more styrene copolymers, and 20% by weight—60% by weight of one or more hydrocolloids of the total weight of the adhesive composition.

8. A method for securing ostomy appliances to the skin and for sealing around an ostomy, for securing wound dressings or wound drainage bandages to the skin, for securing devices for collecting urine to the skin, or for securing orthoses or prostheses to the skin, comprising using an adhesive composition comprising consisting of a homogeneous mixture of 35% by weight—50% by weight of one or more polybutenes having a Flory molecular weight from 50,000 to 60,000, 5% by weight—20% by weight of one or more styrene copolymers, and 20% by weight—60% by weight of one or more hydrocolloids of the total weight of the adhesive composition, wherein the mixture of one or more polybutenes and one or more styrene copolymers and one or more hydrocolloids constitutes the adhesive composition, for securing the ostomy appliances to the skin and for sealing around the ostomy, for securing the wound dressings or the wound drainage bandages to the skin, for securing the devices for collecting urine to the skin, or for securing the orthoses or the prostheses to the skin.

9. The adhesive composition of claim 7, wherein the polybutene is a conjugated butadiene polymer selected from the group consisting of polybutadienes and polyisoprenes.

10. The adhesive composition of claim 7, wherein the styrene copolymer is a styrene-butadiene-styrene block copolymer or a styrene-isoprene-styrene block copolymer.

11. A pressure sensitive adhesive composition suitable for medical purposes by weight of a mixture of polyisobutylene having a Flory molecular weight from 50,000 to 60,000 and styrene-isoprene-styrene block copolymer and 50% by weight of a mixture of hydrocolloids.

12. The adhesive composition of claim 11, wherein the mixture of hydrocolloids comprises gelatine, pectin and CMC.

* * * * *